(12) United States Patent
Duan et al.

(10) Patent No.: US 11,426,059 B2
(45) Date of Patent: Aug. 30, 2022

(54) CONTROL SYSTEM FOR CAPSULE ENDOSCOPE

(71) Applicant: Ankon Medical Technologies (Shanghai) Co., LTD., Shanghai (CN)

(72) Inventors: Xiaodong Duan, Pleasanton, CA (US); Shaobang Zhang, Shanghai (CN)

(73) Assignee: ANKON MEDICAL TECHNOLOGIES (SHANGHAI) CO., LTD., Shanghai (CN)

( * ) Notice: Subject to any disclaimer, the term of this patent is extended or adjusted under 35 U.S.C. 154(b) by 642 days.

(21) Appl. No.: 16/428,956

(22) Filed: May 31, 2019

(65) Prior Publication Data

US 2019/0365210 A1 Dec. 5, 2019

Related U.S. Application Data

(63) Continuation of application No. PCT/CN2019/089670, filed on May 31, 2019.
(Continued)

(51) Int. Cl.
*A61B 1/00* (2006.01)
*A61B 1/04* (2006.01)
(Continued)

(52) U.S. Cl.
CPC .......... *A61B 1/00158* (2013.01); *A61B 1/041* (2013.01); *A61B 5/062* (2013.01); *A61B 34/73* (2016.02); *A61B 90/50* (2016.02); *G01B 7/004* (2013.01); *H01F 7/02* (2013.01); *A61B 2034/733* (2016.02)

(58) Field of Classification Search
CPC ..... A61B 1/00158; A61B 34/73; A61B 1/041; A61B 5/062; A61B 1/00149; A61B 8/4218; A61B 2050/21
See application file for complete search history.

(56) References Cited

U.S. PATENT DOCUMENTS 3,589,102 A * 6/1971 Zelnick ................. B65B 53/066
53/557
4,114,437 A * 9/1978 Krogmann ............. G01C 21/12
73/178 R
(Continued)

FOREIGN PATENT DOCUMENTS

CN 103222842 7/2013
CN 203650520 A 6/2014
(Continued)

OTHER PUBLICATIONS

International search report and Written Opinion for PCT/CN2019/089670.

*Primary Examiner* — John P Leubecker
*Assistant Examiner* — Jae Woo

(57) ABSTRACT

A control device for a capsule endoscope is provided. The control device includes a balance arm device, a permanent magnet, a 2-DOF rotary platform and an examination bed. The bottom of the balance arm device is fixed, and the active end of the balance arm device connects with a boom. The 2-DOF rotary platform is fixed below the boom and the permanent magnet is located in the 2-DOF rotary platform. The examination bed is put below the 2-DOF rotary platform, and the area between the examination bed and the 2-DOF rotary platform is an examination area.

23 Claims, 15 Drawing Sheets

Related U.S. Application Data

(60) Provisional application No. 62/679,790, filed on Jun. 2, 2018.

(51) Int. Cl.
*H01F 7/02* (2006.01)
*A61B 90/50* (2016.01)
*A61B 5/06* (2006.01)
*G01B 7/004* (2006.01)
*A61B 34/00* (2016.01)

(56) References Cited

U.S. PATENT DOCUMENTS

| | | | | |
|---|---|---|---|---|
| 5,474,264 A * | 12/1995 | Lund | | G01S 17/02 356/152.3 |
| 6,208,937 B1 * | 3/2001 | Huddle | | G01C 21/165 701/472 |
| 10,750,935 B2 * | 8/2020 | Kawano | | A61B 1/00045 |
| 2004/0246469 A1 * | 12/2004 | Hirose | | A61B 10/00 356/139.07 |
| 2006/0158373 A1 * | 7/2006 | Kamei | | G01S 19/43 342/357.41 |
| 2009/0326322 A1 * | 12/2009 | Diolaiti | | A61B 1/008 600/112 |
| 2013/0096874 A1 * | 4/2013 | Laabs | | G01C 15/00 702/150 |
| 2013/0110128 A1 * | 5/2013 | Schostek | | B25J 19/0008 606/130 |
| 2013/0267788 A1 * | 10/2013 | Duan | | G06T 7/62 600/300 |
| 2014/0288416 A1 * | 9/2014 | Mahoney | | A61B 1/00158 600/118 |
| 2015/0018615 A1 * | 1/2015 | Duan | | A61B 1/00006 600/109 |
| 2015/0380140 A1 * | 12/2015 | Duan | | A61B 1/041 600/109 |
| 2016/0022124 A1 * | 1/2016 | Li | | A61B 1/041 600/118 |
| 2016/0135662 A1 * | 5/2016 | Hatakeyama | | A61B 90/96 606/130 |
| 2016/0287058 A1 * | 10/2016 | Ye | | A61B 1/00158 |
| 2017/0035520 A1 * | 2/2017 | Duan | | A61B 17/0218 |
| 2018/0084975 A1 * | 3/2018 | Duan | | A61B 1/00158 |
| 2018/0084976 A1 * | 3/2018 | Duan | | A61B 34/73 |
| 2018/0164416 A1 * | 6/2018 | Ekengren | | G01S 17/10 |
| 2018/0296289 A1 * | 10/2018 | Rodriguez-Navarro | | A61B 1/00045 |
| 2019/0282076 A1 * | 9/2019 | Duan | | A61B 1/0655 |
| 2019/0293450 A1 * | 9/2019 | Hino | | G05D 1/101 |
| 2019/0365210 A1 * | 12/2019 | Duan | | A61B 1/041 |
| 2019/0365211 A1 * | 12/2019 | Duan | | A61B 90/50 |
| 2020/0315895 A1 * | 10/2020 | Song | | A61B 5/112 |
| 2020/0357108 A1 * | 11/2020 | Zhou | | G06T 7/74 |
| 2021/0240059 A1 * | 8/2021 | Ma | | F16M 11/205 |
| 2021/0341566 A1 * | 11/2021 | Huang | | G06K 9/6288 |

FOREIGN PATENT DOCUMENTS

| | | |
|---|---|---|
| CN | 105615817 | 6/2016 |
| CN | 105962876 A | 9/2016 |
| CN | 106691366 | 5/2017 |
| CN | 107307838 | 11/2017 |
| JP | 2008503310 A | 2/2008 |
| WO | 2010044053 A | 4/2010 |

* cited by examiner

CONTROL SYSTEM FOR CAPSULE ENDOSCOPE

CROSS REFERENCE TO RELATED APPLICATIONS

The present invention takes priority of a U.S. provisional application 62/679,790 filed on Jun. 2, 2018. The disclosure is included in this application in its entirety.

FIELD OF INVENTION

The invention generally relates to a medical device, particularly refers to a control device for a capsule endoscope.

BACKGROUND

Depending on the advantages of no pain and no invasion in examination, a capsule endoscopy has been gradually applied in the clinical diagnosis of various diseases. Generally, the capsule endoscope contains a small magnet. After the capsule endoscope is swallowed into the digestive tract of a subject, an external magnetic device is used to control the capsule endoscope through magnetic induction to move and rotate in the digestive tract. The position and orientation of the capsule endoscope is effectively controlled to accurately determine the conditions of examination areas.

Existing control device of the capsule endoscope comprises a rack, a rotating device, a C-arm (moving arm), a permanent magnet, and a driving device. The rotating device is equipped on the rack, the C-arm is fixed on the rotating device, and the permanent magnet is installed at the end of the C-arm. When the capsule endoscope is taken orally by the subject, the capsule endoscope will be controlled by the permanent magnet. The driving device is electrically connected with the rotating device and the C-arm, and receives external control commands to control the movement of the rotating device, the C-arm and the permanent magnet. The position and orientation of the capsule endoscope inside the digestive tract is controlled by the permanent magnet. In order to facilitate examination, an examination bed that is movable is provided below the rotating device and the C-arm for carrying the subject. The control device employs an electrical control method, wherein the driving device is used to control the rotation and movement of the rotating device and the C-arm. Since the C-arm is fixed on the rotating device, when the rotating device rotates, the C-arm is driven to rotate together, and at the same time, the posture of the C-arm can be adjusted to change the position and posture of the permanent magnet, so as to ensure that the permanent magnet can reach all positions of the examination areas.

In general, to ensure effective control of the capsule endoscope swallowed into the digestive tract of the subject, the permanent magnet suspended below the C-arm requires a certain volume and weight, e.g., 30-50 kg. At this moment, the C-arm always bears the weight of the heavy permanent magnet; however, as a precision machine, the C-arm has a limited loading capacity and is costly. Long-term loading of the heavy permanent magnet will cause the C-arm to be deformed or even damaged, thereby affecting the examination accuracy.

Further, in the above solution, the control of the capsule endoscope by the control device needs to be transmitted through human-control terminal-computer-server-motor-permanent magnet, so that the overall system structure is complicated and the operation is inconvenient. In addition, the C-arm can only drive the permanent magnet to rotate in a fixed circular area with the rotation of the rotating device, so the examination areas are restricted.

Therefore, it is necessary to provide a control device for the capsule endoscope that features simplified structure, easy operation, low cost and high efficiency.

SUMMARY OF THE INVENTION

The present invention discloses a control device for a capsule endoscope, comprising a balance arm device, a permanent magnet, a 2-DOF rotary platform and an examination bed; wherein the bottom of the balance arm device is fixed, and the active end of the balance arm device connects with a boom; wherein the 2-DOF rotary platform is fixed below the boom and the permanent magnet is located in the 2-DOF rotary platform; wherein the examination bed is put below the 2-DOF rotary platform, and the area between the examination bed and the 2-DOF rotary platform is an examination area.

The present invention discloses a control device for a capsule endoscope, comprising: a balance arm device, a permanent magnet and an examination bed; wherein the bottom of the balance arm device is fixed, and the active end of the balance arm device connects with a boom; wherein the permanent magnet is fixed below the boom; wherein the examination bed is put below the permanent magnet, and the area between the examination bed and the permanent magnet is an examination area.

It is one object of the present invention that the balance arm device is a pneumatic balance arm or a spring assisted balance arm.

It is another object of the present invention that the 2-DOF rotary platform is a full-manual rotary platform or an electrically controlled rotary platform.

It is another object of the present invention that the control device uses the balance arm device in conjunction with the 2-DOF rotary platform to provide a 5-DOF movement range, and realize free control of a capsule endoscope through control of the permanent magnet.

DETAILED DESCRIPTION

Figure 1:
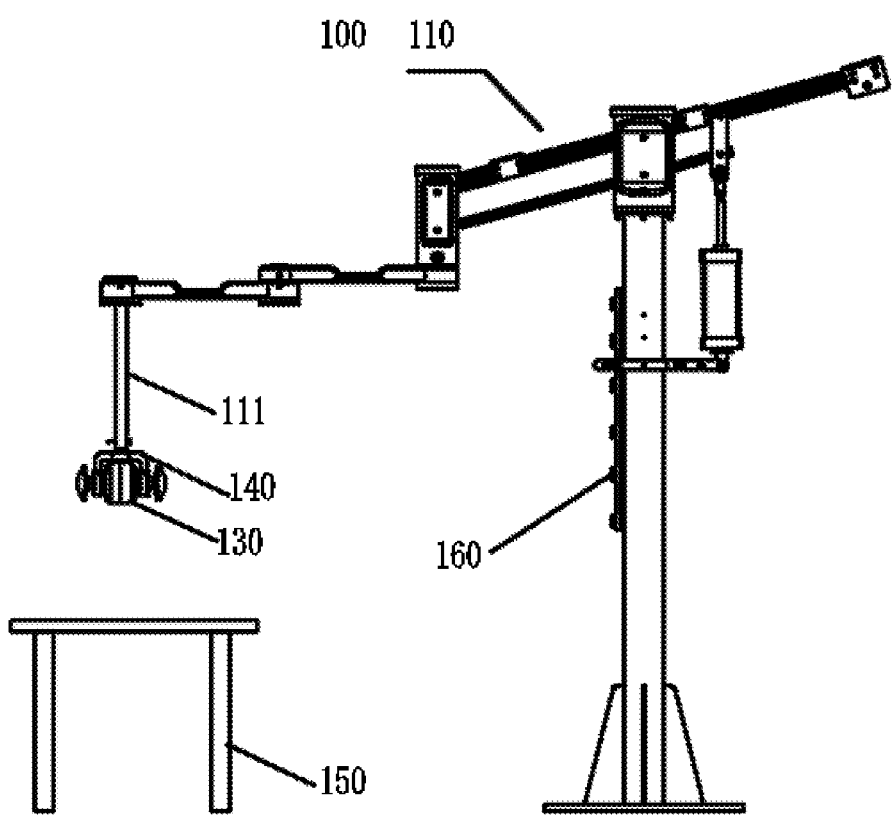
FIG. 1 shows a schematic view of a control device for a capsule endoscope in accordance with the first embodiment of the present invention.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Referring to FIG. 1, which shows a schematic view of a control device for a capsule endoscope in accordance with the first embodiment of the present invention. As shown in the figure, the control device for the capsule endoscope 100 comprises a balance arm device 110, a permanent magnet 130, a 2-DOF rotary platform 140, an examination bed 150 and a magnetic sensor array 160. The bottom end of the balance arm device 110 is fixed, and the active end of the balance arm device 110 connects with a boom 111. The 2-DOF rotary platform 140 is linked below the boom 111 and the permanent magnet 130 is located in the 2-DOF rotary platform 140. The examination bed 150 is put below the 2-DOF rotary platform 140 for convenient examination of the subject lying on the bed. The area between the examination bed 150 and the 2-DOF rotary platform 140 is the examination area. The magnetic sensor array 160 comprises a plurality of magnetic sensors that are used to detect spatial positions of the permanent magnet 130. The spatial positions of the permanent magnet 130 comprise three-dimensional position and two-dimensional direction. At the time of examination, the capsule endoscope containing a small magnet enters the digestive tract of the subject, and with the assistance of the balance arm device 110, the permanent magnet 130 acts on the small magnet inside the capsule endoscope to drive the capsule endoscope to move within the digestive tract.

Figure 20:
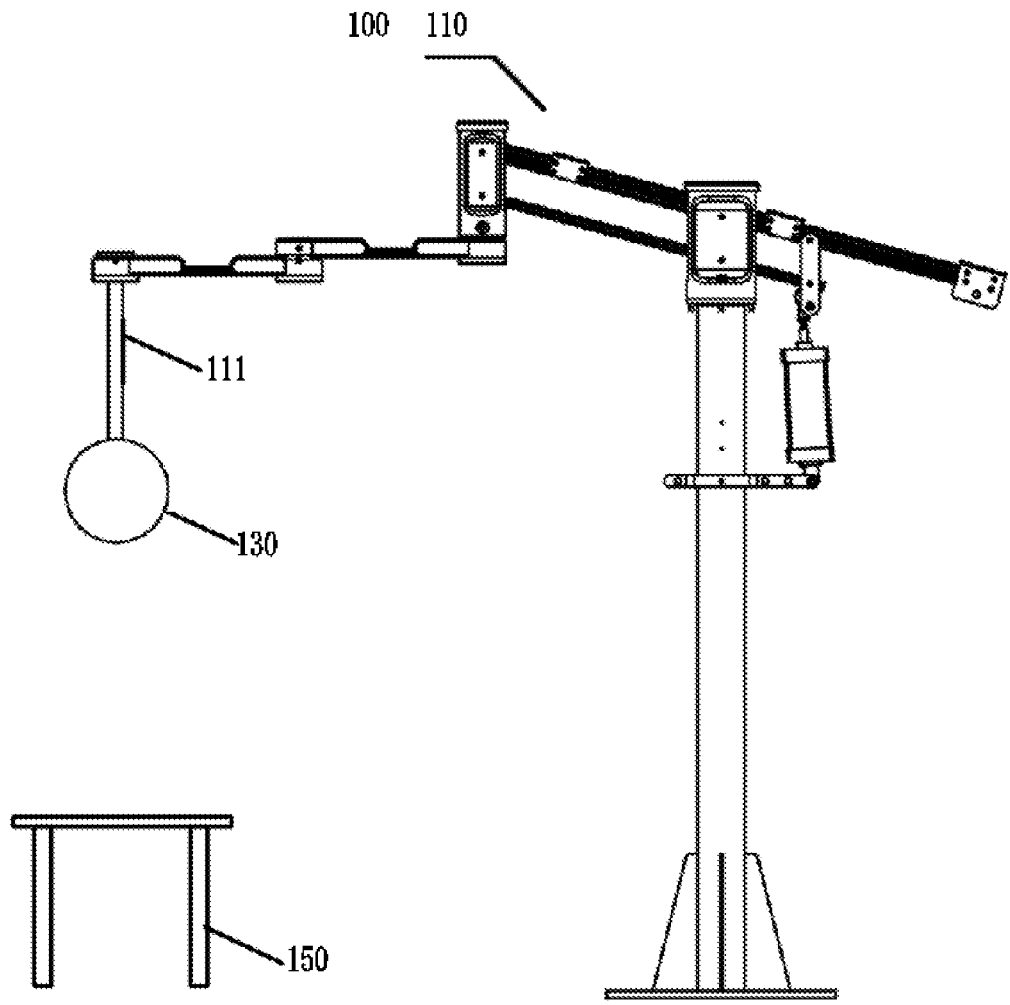
FIG. 20 shows a schematic view of a control device for a capsule endoscope in accordance with one embodiment of the present invention.
Figure 21:
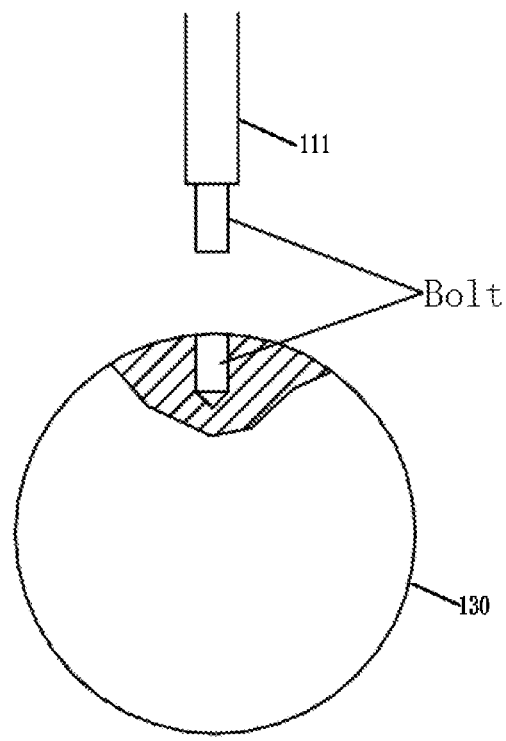
FIG. 21 is a schematic view showing a connection between a permanent magnet and a boom.
Figure 22:
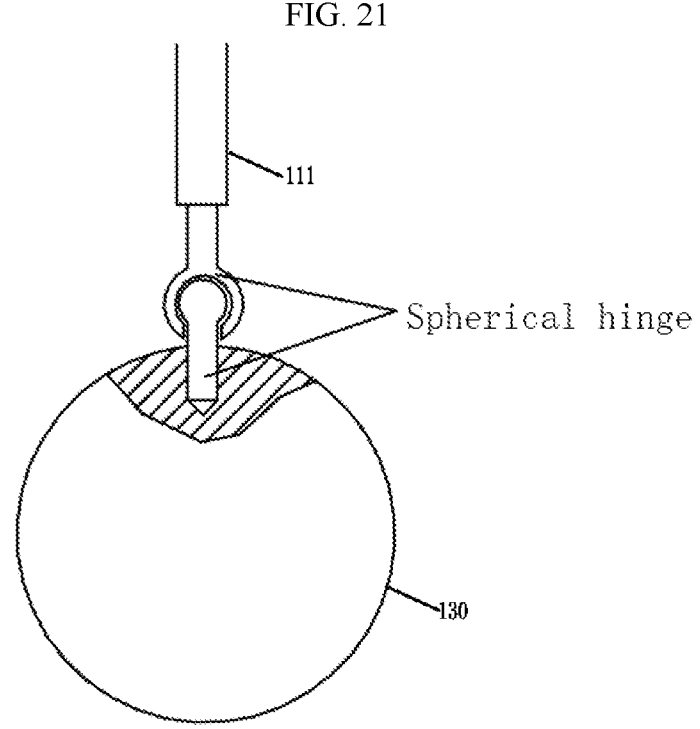
FIG. 22 is a schematic view showing a connection between a permanent magnet and a boom.

In an embodiment, the control device for the capsule endoscope 100 may not include the 2-DOF rotary platform 140, as shown in FIG. 20. That is, the control device for the capsule endoscope 100 includes the balance arm device 110, the permanent magnet 130, and the examination bed 150. The bottom end of the balance arm device 110 is fixed, and the active end of the balance arm device 110 connects with a boom 111. The permanent magnet 130 is located below the boom 111. The examination bed 150 is disposed under the permanent magnet 130, and the area between the examination bed 150 and the permanent magnet 130 is the examination area to be detected. The permanent magnet 130 rotates in one or more degrees of freedom. In one embodiment, the permanent magnet 130 is bolted to the boom 111, as shown in FIG. 21. In one embodiment, the permanent magnet 130 is connected to the boom 111 through a spherical hinge, as shown in FIG. 22. In the embodiment, the permanent magnet 130 is controlled by manpower.

According to a magnetic dipole model, the magnetic sensor array 160 utilizes the plurality of magnetic sensors to detect the spatial positions of the permanent magnet 130. According to a nonlinear least-squares algorithm, the three-dimensional position and two-dimensional direction of the permanent magnet 130 are obtained.

For example, if the central position of the permanent magnet 130 is denoted by (a, b, c) and the magnetization direction of the permanent magnet 130 is denoted by (m, n, p), according to the magnetic dipole model, the magnetic field intensity $(B_{1x}, B_{1y}, B_{1z})$ sensed by the magnetic sensors at the position $(x_1, y_1, z_1)$ can be expressed as:

$$B_{1x} = B_T \left\{ \frac{3[m(x_1-a)+n(y_1-b)+p(z_1-c)] \cdot (x_1-a)}{R_1^5} - \frac{m}{R_1^3} \right\}$$

$$B_{1y} = B_T \left\{ \frac{3[m(x_1-a)+n(y_1-b)+p(z_1-c)] \cdot (y_1-b)}{R_1^5} - \frac{n}{R_1^3} \right\}$$

$$B_{1z} = B_T \left\{ \frac{3[m(x_1-a)+n(y_1-b)+p(z_1-c)] \cdot (z_1-c)}{R_1^5} - \frac{p}{R_1^3} \right\}$$

$$m^2 + n^2 + p^2 = 1$$

Wherein, $B_T$ is a constant related to the volume and magnetization of the permanent magnet 130, and $R_1$ is the Euclidean distance between the position of the magnetic sensor and the position of the permanent magnet 130.

If multiple magnetic sensors are used to form the magnetic sensor array 160, the position $(x_1, y_1, z_1)$ of each magnetic sensor and the measurements $B_{1x}, B_{1y}, B_{1z}$ of each magnetic sensor are known, and the position (a, b, c) and direction vector (m, n, p) of the permanent magnet 130 are unknown, multiple equations can be listed to form an equations set; since this is a nonlinear problem, a target error function is built based on the equations set, and use a nonlinear least-squares algorithm to solve the position and direction of the permanent magnet 130.

In the embodiment, to make it convenient for the operator to judge the rotation angle of the permanent magnet 130, the permanent magnet 130 performs two-dimensional rotation within the 2-DOF rotary platform 140. At this moment, it is necessary to make sure that the initial direction of the rotary platform 140 is unchanged. When the balance arm device 110 adjusts the spatial position, the 2-DOF rotary platform 140 may have a deflection and the angle of deflection can be superimposed on the rotation angle of the permanent magnet 130. In order to improve the control precision of the permanent magnet 130 on the capsule endoscope, the angle of deflection of the 2-DOF rotary platform 140 needs to be compensated.

Figure 10:
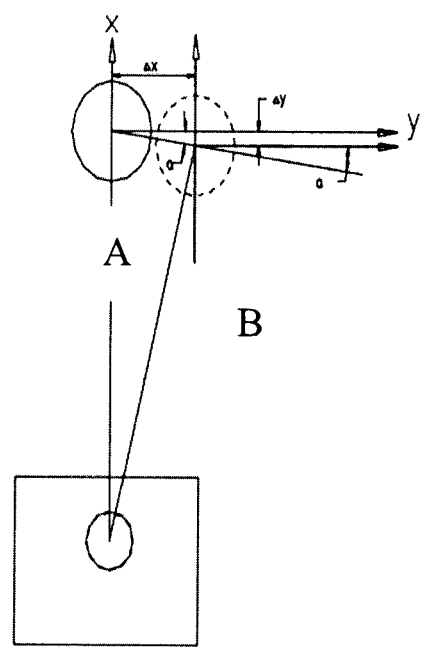
FIG. 10 shows a schematic view of calculating a compensation angle of the 2-DOF rotary platform according to displacement of the permanent magnet.

In the embodiment, the magnetic sensor array 160 detects the position and direction of the permanent magnet 130, and calculates the compensation angle of the 2-DOF rotary platform 140 according to the displacement of the permanent magnet 130. As shown in FIG. 10, the balance arm device 110, the permanent magnet 130 end the 2-DOF rotary platform 140 are moved from position A to position B, the displacements of the permanent magnet 130 in the x and y directions are $\Delta x$ and $\Delta y$, and the compensation angle $\alpha$ of the 2-DOF rotary platform 140 is calculated as $\tan \alpha = \Delta y / \Delta x$.

In the embodiment, the 2-DOF rotary platform 140 and the permanent magnet 130 are located at the end of the balance arm device 110. When the 2-DOF rotary platform 140 is moved horizontally, the permanent magnet 130 has a deflection to the geodetic coordinate system. To prevent the permanent magnet 130 from deflection to the geodetic coordinate system, the horizontal deflection angle of the permanent magnet 130 is compensated. When the magnetic sensor array 160 detects a certain horizontal movement direction of the permanent magnet 130, the horizontal orientation of the magnet NS pole should be consistent with the horizontal movement direction. At this time, the permanent magnet 130 will rotate from the original horizontal angle to the detected movement direction angle, and during movement, the deflection of the permanent magnet 130 to the geodetic coordinate system is compensated. The compensated deflection angle of the permanent magnet 130 is a negative deflection angle of the 2-DOF rotary platform 140.

When the capsule endoscope is at the lower gastric wall of the subject, the tangential direction of the permanent magnet 130 rotating away from the lower gastric wall is opposite to the movement direction of the permanent magnet 130; when the capsule endoscope is at the upper gastric wall of the subject, the tangential direction of the permanent magnet 130 rotating away from the upper gastric wall is consistent with the movement direction of the permanent magnet 130; the speed of rotation and movement of the permanent magnet 130 follows: $v = \omega * L$, wherein v is the average movement speed of the permanent magnet 130, $\omega$ is the average rotation angular speed of the permanent magnet 130, and L is the length of the capsule endoscope.

Figure 11:
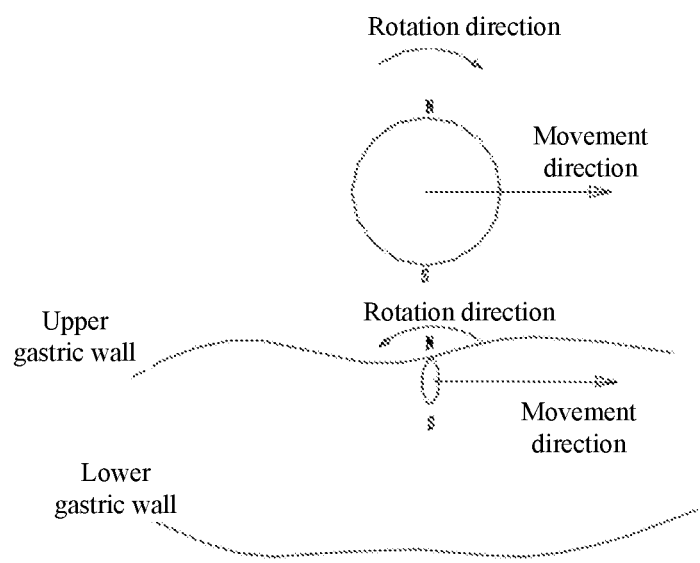
FIGS. 11 and 12 show schematic views of movement of the capsule endoscope at the upper gastric wall under the control of the permanent magnet rotating and moving.
Figure 12:
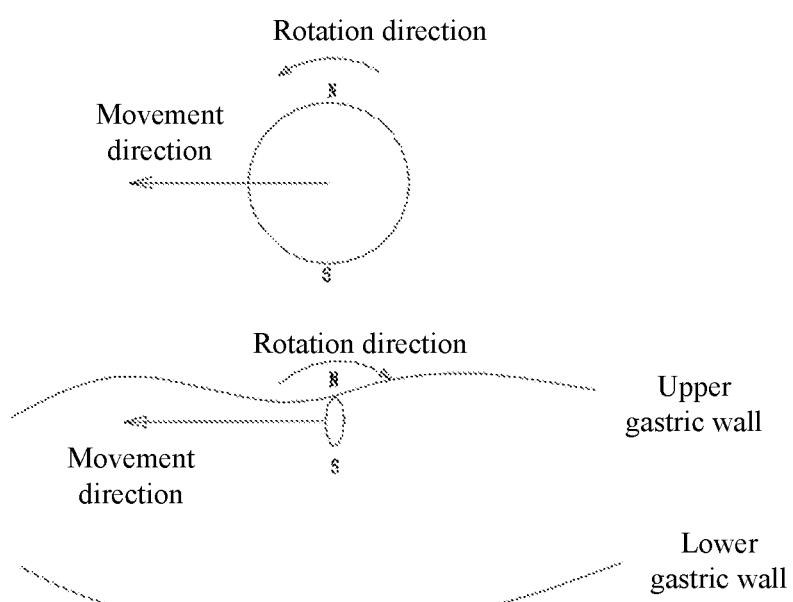

Referring to FIGS. 11 and 12, which show schematic views of movement of the capsule endoscope at the upper gastric wall under the control of the permanent magnet 130 rotating and moving. As shown in FIG. 11, when the permanent magnet 130 moves to the right and rotates to the right (clockwise), the capsule endoscope moves to the right and rotates to the left (counterclockwise); as shown in FIG. 12, when the permanent magnet 130 moves to the left and rotates to the left (counterclockwise), the capsule endoscope moves to the left and rotates to the right (clockwise). That is, the movement direction of the capsule endoscope coincides with the movement direction of the permanent magnet 130, and the rotation direction of the capsule endoscope is opposite to the rotation direction of the permanent magnet 130.

Figure 13:
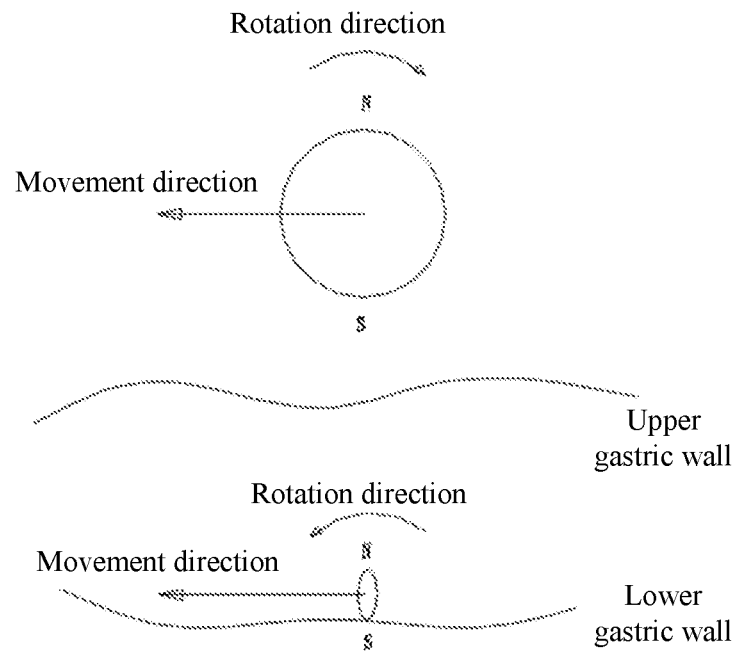
FIGS. 13 and 14 show schematic views of movement of the capsule endoscope at the lower gastric wall under the control of the permanent rotating and moving.
Figure 14:
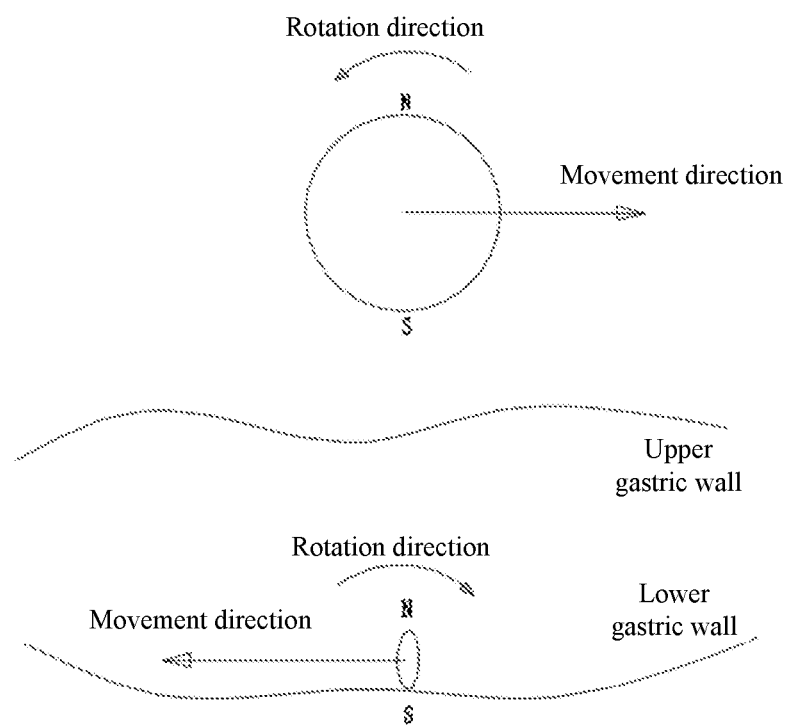

Referring to FIGS. 13 and 14, which show schematic views of movement of the capsule endoscope at the lower gastric wall under the control of the permanent magnet 130 rotating and moving. As shown in FIG. 13, when the permanent magnet 130 moves to the left and rotates to the right (clockwise), the capsule endoscope moves to the left and rotates to the left (counterclockwise); as shown in FIG. 14 when the permanent magnet 130 moves to the right and rotates to the left (counterclockwise), the capsule endoscope moves to the left and rotates to the right (clockwise). That is, the rotation direction of the capsule endoscope is opposite to the rotation direction of the permanent magnet 130.

In the present invention, when the control device 100 is in use, the balance arm device 110 counterbalances the weight of the permanent magnet 130 and the 2-DOF rotary platform 140, so that the 2-DOF rotary platform 140 and the permanent magnet 130 only need to overcome the mechanical friction force of the rotating shaft of the balance arm device 110 when moving in the direction of gravity and moving in horizontal direction. The friction force of the rotating shaft is far less than the gravity, so the 2-DOF rotary platform 140 and the permanent magnet 130 can be easily operated. By positioning the permanent magnet 130 in three dimensional coordinates and positioning the permanent magnet 130 in rotation angles via the 2-DOF rotary platform 140, the operator can control the position and orientation of the capsule endoscope through the permanent magnet 130. The space occupied by the control device 100 is greatly reduced, with no restriction on the posture of the subject, who can be lying or sitting or standing, and the implementation cost is lower.

Figure 2:
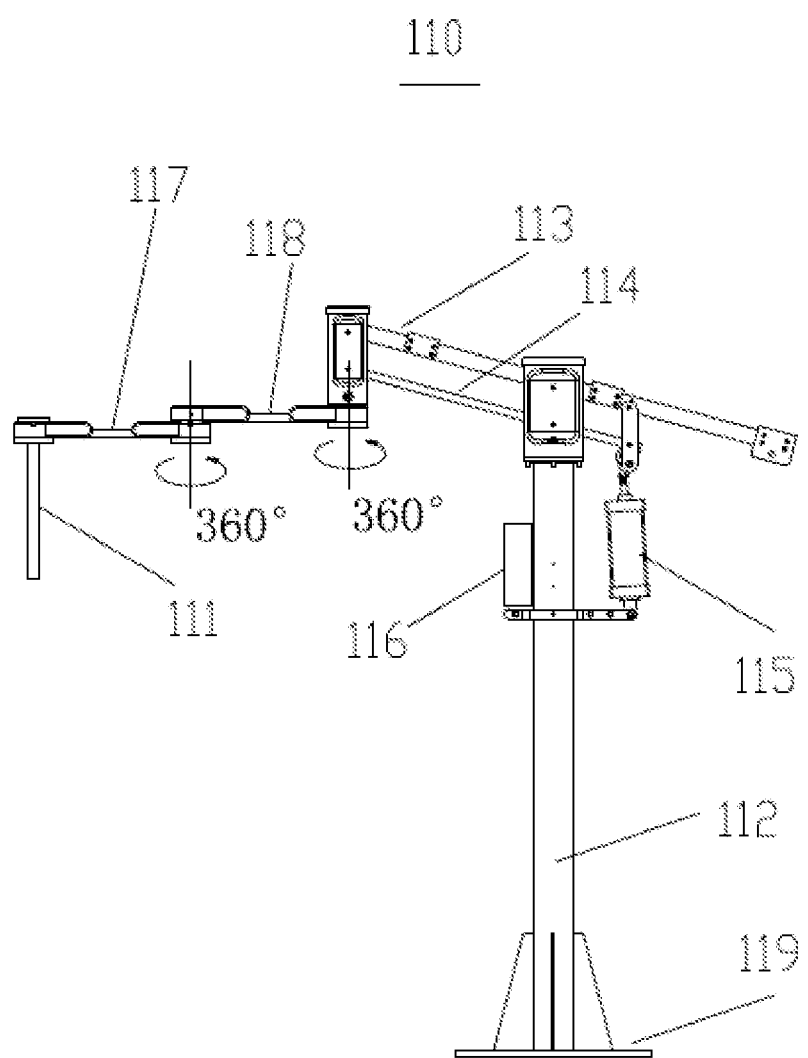
FIG. 2 shows a schematic view of a pneumatic balance arm of FIG. 1.
Figure 15:
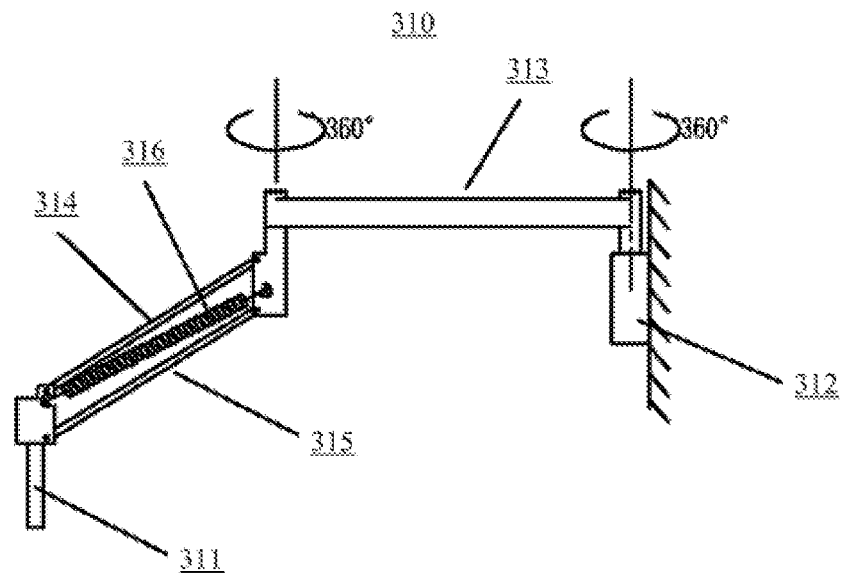
FIG. 15 shows a schematic view of a spring assisted balance arm.
Figure 16:
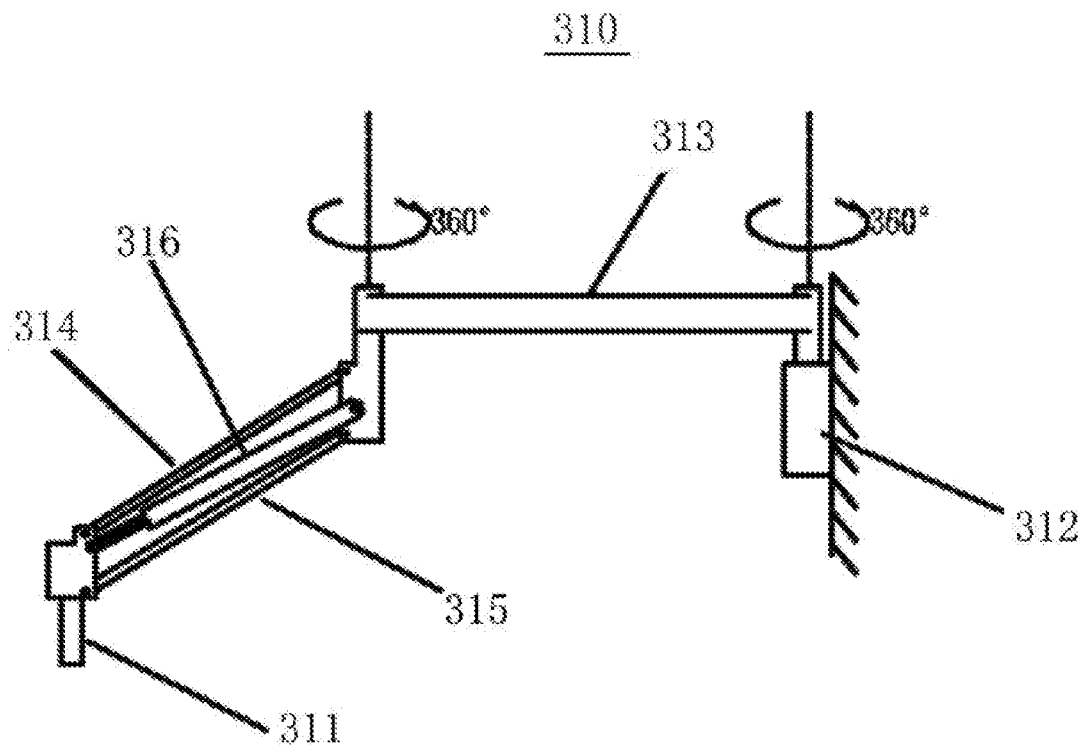
FIG. 16 is a schematic view showing the structure of a spring assist arm device of another embodiment.

The balance arm device 110 can be a pneumatic balance arm 110 that uses a balance cylinder 115 to balance the boom 111, as shown in FIG. 2, or may be a spring assisted balance arm 310 that uses a common spring or a gas spring to balance the boom 111, as shown in FIG. 15.

FIG. 2 shows a schematic view of the pneumatic balance arm 110 of FIG. 1. The pneumatic balance arm 110 comprises a column 112 and a chassis 119 for providing support. A upper balance arm 113 and a lower balance arm 114 that are parallel to each other and have an angle to the column 112 are attached to the top of the column 112; the balance cylinder 115 is hingely fixed on a side of the column 112 and is located below the upper balance arm 113 and the lower balance arm 114, a tracheal piston of the balance cylinder 115 is connected to the upper balance arm 113 and the lower balance arm 114 through a hinge for providing impetus for the upper balance arm 113 and the lower balance arm 114 moving upward or downward. Under the telescopic pull of tracheal piston action of the balance cylinder 115, the upper balance arm 113 and the lower balance arm 114 can deflect 360 degrees vertically and horizontally. That is, when the tracheal piston of the balance cylinder 115 contracts, the upper balance arm 113 and the lower balance arm 114 are tilted up, and when the tracheal piston of the balance cylinder 115 is stretched, the upper balance arm 113 and the lower balance arm 114 are lowered. The magnetic sensor array 160 is fixed on the column 112.

A control box 116 is also fixed on other side of the column 112. The control box 116 is electrically connected to the balance cylinder 115 for controlling the cylinder piston to move up and down. Under the control of the control box 116, the piston of the balance cylinder 115 moves up and down to drive the upper balance arm 113 and the lower balance arm 114 to move up and down in the vertical direction.

The other ends of the upper balance arm 113 and the lower balance arm 114 are connected to the rear terminal arm 118 and the front terminal arm 117. The rear terminal arm 118 is located between the front terminal arm 117 and the upper balance arm 113 and lower balance arm 114. Wherein, the rear terminal arm 118 is pivotally connected to the upper balance arm 113 and the lower balance arm 114, and the rear terminal arm 118 can rotate horizontally 360 degrees along the pivot. The front terminal arm 117 and the rear terminal arm 118 are also pivotally connected, and the front terminal arm 117 can rotate horizontally 360 degrees along the pivot. Specifically, the rear terminal arm 118 or the front terminal arm 117 can be driven to rotate horizontally 360 degrees along the axis, by a human arm or mechanical arm. The boom 111 is perpendicularly connected to the other end of the front terminal arm 117. In the embodiment, the upper balance arm 113, the lower balance arm 114, the rear terminal arm 118, and the front terminal arm 117 are both rigid arms. According to one embodiment of the prevent invention, the rear terminal arm 118 has the same length as the front terminal arm 117. According to another embodiment of the present invention, the rear terminal arm 118 and the front terminal arm 117 are different in length.

In this way, the rigid arm of the pneumatic balance arm 110 can bear the weight of the permanent magnet 130 fixed at the end of the boom 111 and overcome the gravity to move the permanent magnet 130 up and down, left and right, and achieve gravity balancing.

The chassis 119 can either be the fixed chassis shown in FIG. 2, or a movable chassis (not shown in FIG. 2) with wheels on the bottom. The wheels of the movable chassis can be moved and locked. A balance weight object can be configured on the movable chassis to balance the weight of the control device 100, so as to avoid that the movable chassis cannot be fixed because of too large weight of the permanent magnet 130.

Figure 3:
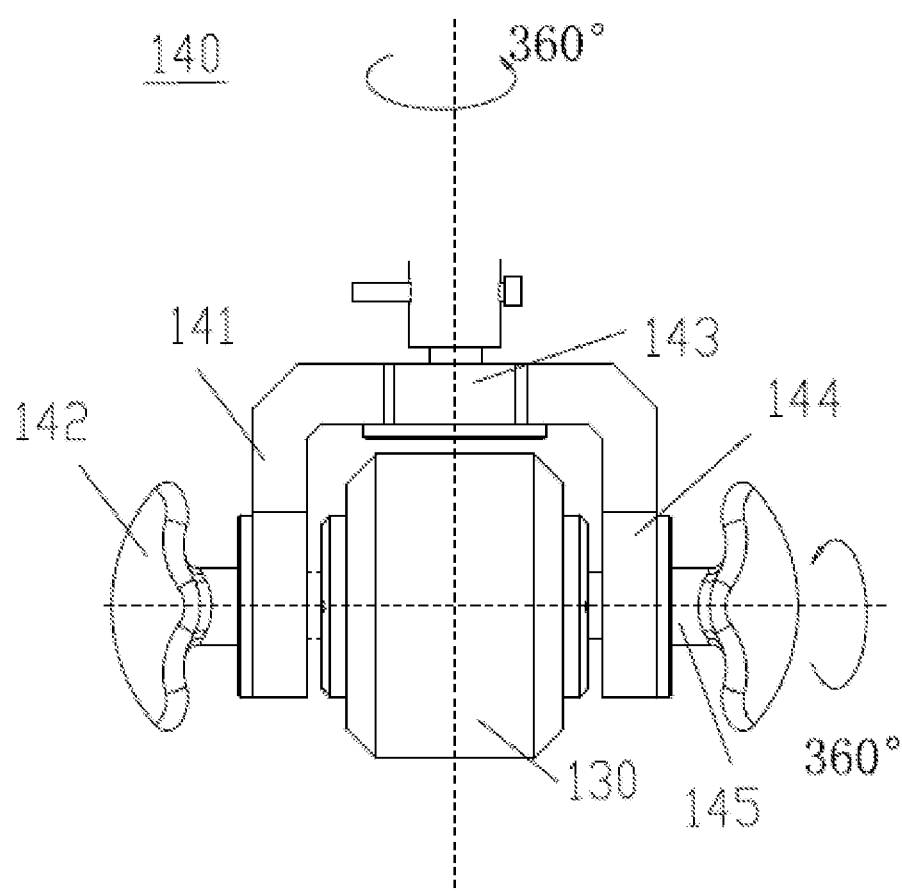
FIG. 3 shows a schematic view of a 2-DOF rotary platform of FIG. 1.

FIG. 3 shows a schematic view of the 2-DOF rotary platform 140 of FIG. 1. The 2-DOF rotary platform 140 is a full-manual rotary platform, comprising an upper enclosure 141. The upper enclosure 141 is symmetrical along the central axis and comprises a horizontal part and two vertical parts that are perpendicular to the horizontal part. A bearing 143 passing through the central axis is fitted at the horizontal part and provides 360-degree rotation in the horizontal direction. Each of the vertical parts is also fitted with a bearing 144 and a horizontal rod 145 passes through the bearings 144. Two handles 142 are fitted on both ends of the horizontal rod 145 which is sleeved by the permanent magnet 130. The 2-DOF rotary platform 140 is fully manual. Due to the presence of bearings, a vertical rotation of the handles 142 can rotate the permanent magnet 130 vertically and maintain vertical angle positioning at any time; a horizontal rotation of the two handles 142 can rotate the permanent magnet 130 horizontally, and maintain angle positioning. In use, the position of movement is manually adjusted. If the 2-DOF rotary platform 140 is a fully manual rotary platform, the compensation angle α of the rotary platform 140 is manually compensated by the operator during operation.

Figure 4:
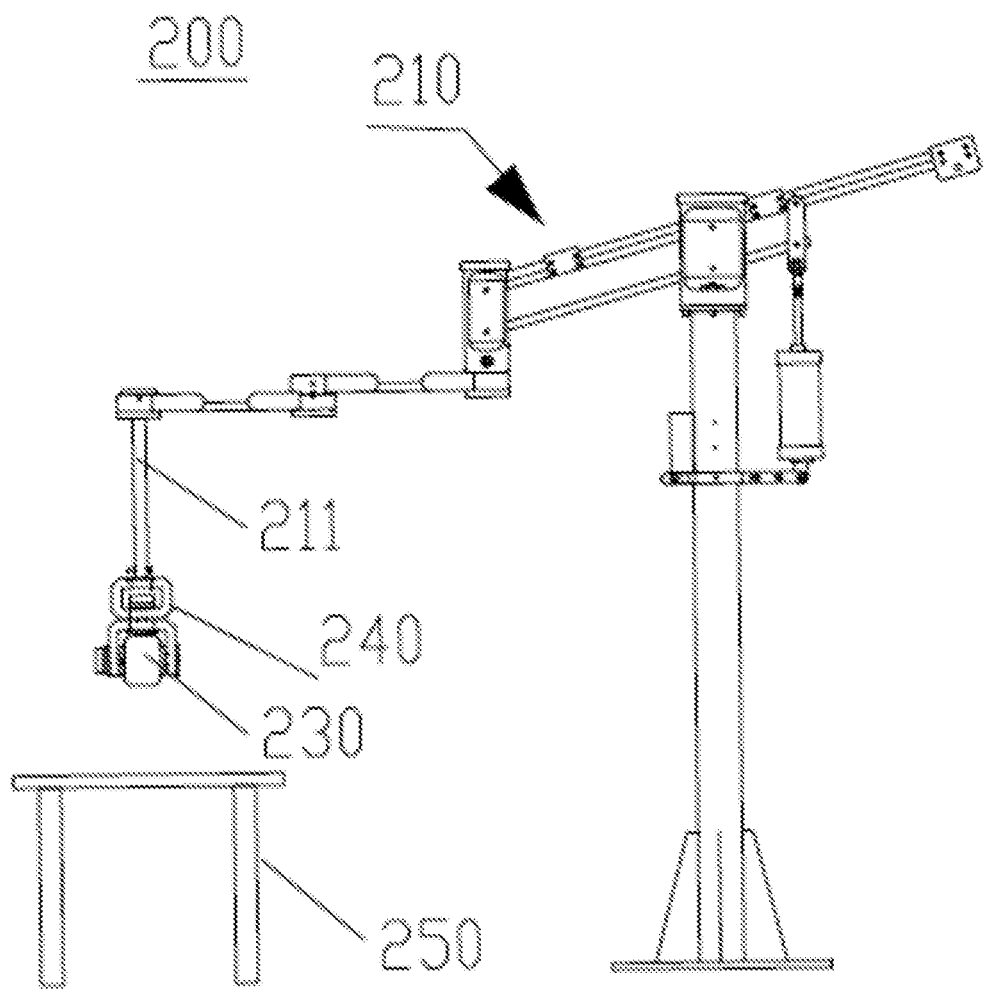
FIG. 4 shows a schematic view of the control device for the capsule endoscope in accordance with the second embodiment of the present invention.

FIG. 4 shows a schematic view of the control device for the capsule endoscope in accordance with the second embodiment of the present invention. As shown in the FIG. 4, the control device 200 comprises a pneumatic balance arm 210, a permanent magnet 230, a 2-DOF rotary platform 240 and an examination bed 250. The pneumatic balance arm 210 has its bottom fixed, and the active end of the pneumatic balance arm 210 connects with a boom 211. The 2-DOF rotary platform 240 is linked below the boom 211 and the permanent magnet 230 is located in the 2-DOF rotary platform 240. The examination bed 250 is put below the 2-DOF rotary platform 240 for convenient examination of the subject lying on the bed. At the time of examination, the capsule endoscope containing a small magnet enters the digestive tract of the subject, and with the assistance of the balance arm device 210, the permanent magnet 230 acts on the small magnet inside the capsule endoscope to drive the capsule endoscope to move within the digestive tract. The capsule endoscope control device 200 can also comprise a magnetic sensor array 160, which is not shown in FIG. 4.

Figure 5:
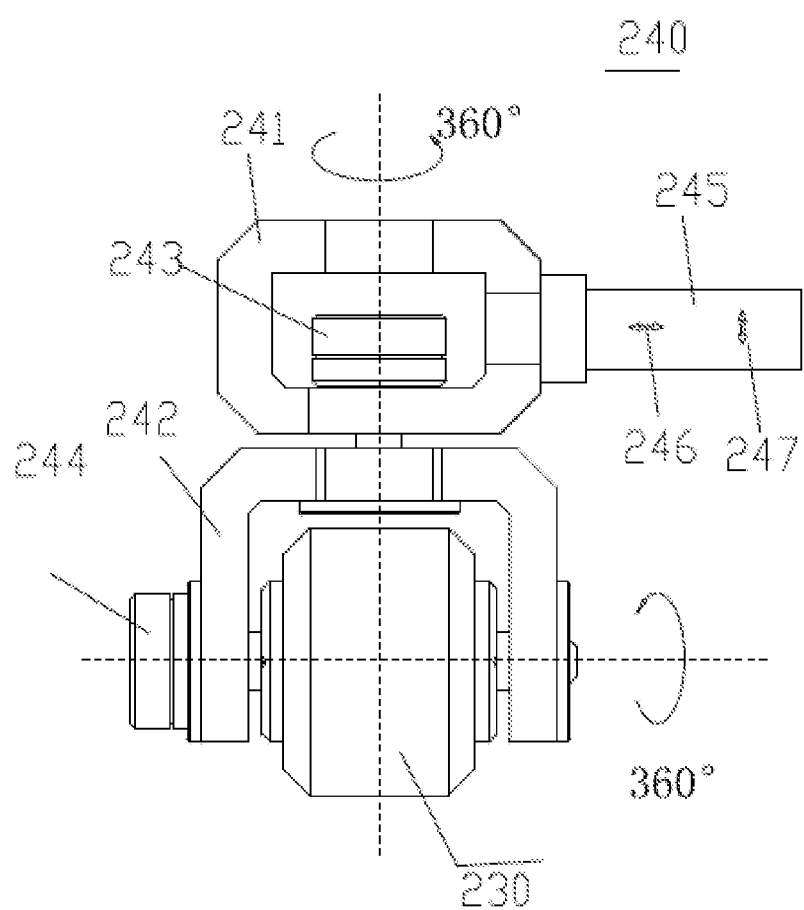
FIG. 5 shows a schematic view of the 2-DOF rotary platform of FIG. 4.
Figure 18:
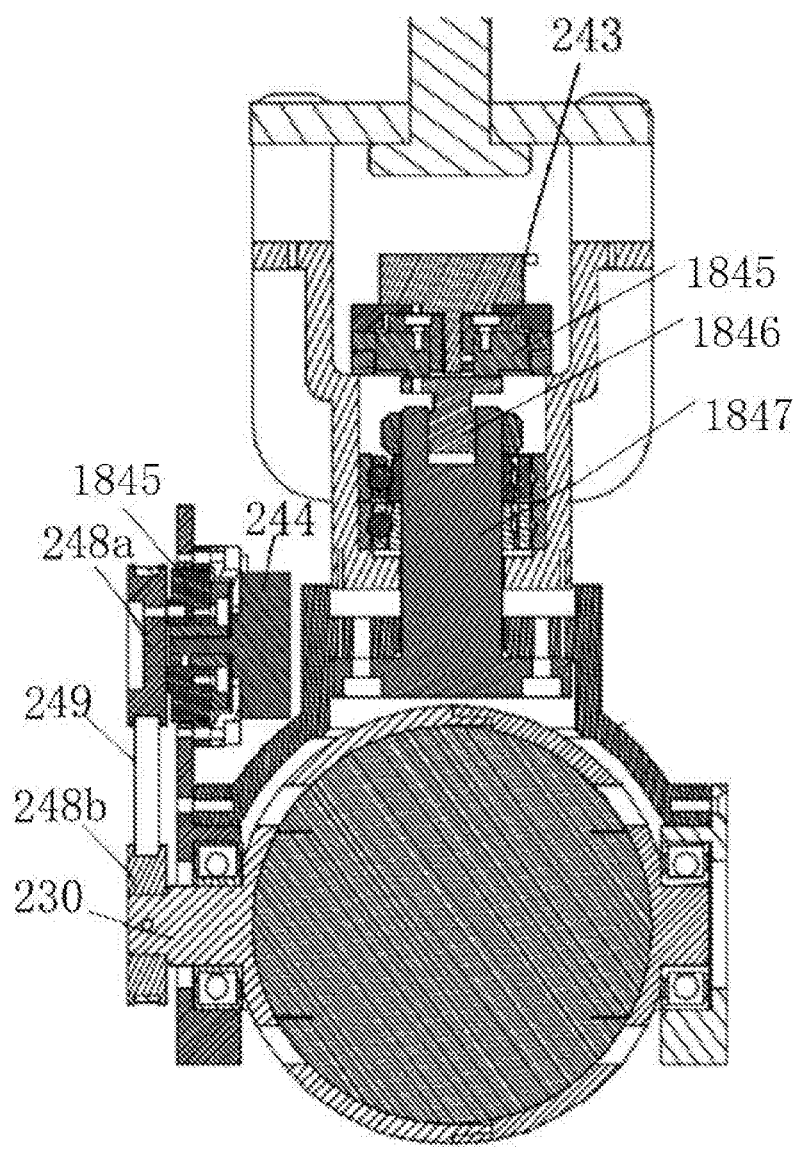
FIG. 18 is a view showing an exemplar connection structure of the first motor and the second motor.

FIG. 5 shows a schematic view of the 2-DOF rotary platform 240 of FIG. 4. The rotary platform 240 is an electrically controlled rotary platform, comprising a first enclosure 241 and second enclosure 242 that are connected to each other. The first enclosure 241 has a first motor 243 therein which provides a 360-degree rotation along the longitudinal axis; the second enclosure 242 has a second motor 244 therein which provides a 360-degree rotation along the horizontal axis. As shown in FIG. 18, the first motor 243 is connected to one end of the main shaft 1847 via the harmonic reducer 1845 and the coupling 1846, and the other end of the main shaft 1847 is connected to the second enclosure 242, and then passes through the first motor 243. The second enclosure 242 is driven to rotate 360 degrees in the longitudinal direction. The second motor 244 is connected to the permanent magnet 230 via the harmonic reducer 1845, the synchronous wheel and the timing belt 249, and further drives the permanent magnet 230 to rotate 360 degrees in the horizontal axis direction by the second motor 244. Among them, the synchronous wheel includes a primary synchronous wheel 248a and a secondary synchronous wheel 248b. A control handle 245 is fitted on one side of the first enclosure 241. The control handle 245 provides a horizontal rotation button 246 and a vertical rotation button 247. The control handle 245 on the rotary platform 240 can be used to control the permanent magnet 230 to adjust spatial positions. The horizontal rotation button 246 and the vertical rotation button 247 on the control handle 245 control the permanent magnet 230 to rotate horizontally and vertically, achieving a 2-DOF rotation positioning. The electrically controlled rotary platform can further reduce labor intensity. At the same time, the pneumatic balance arm 210 drives the permanent magnet 230 connected to the boom 211 to move in a three-dimensional space, thereby driving the capsule endoscope in the digestive tract to move in five degrees of freedom. If the 2-DOF rotary platform 240 is electrically controlled, the compensation angle α of the rotary platform 240 is automatically compensated by the first motor 243 and the second motor 244.

Figure 6:
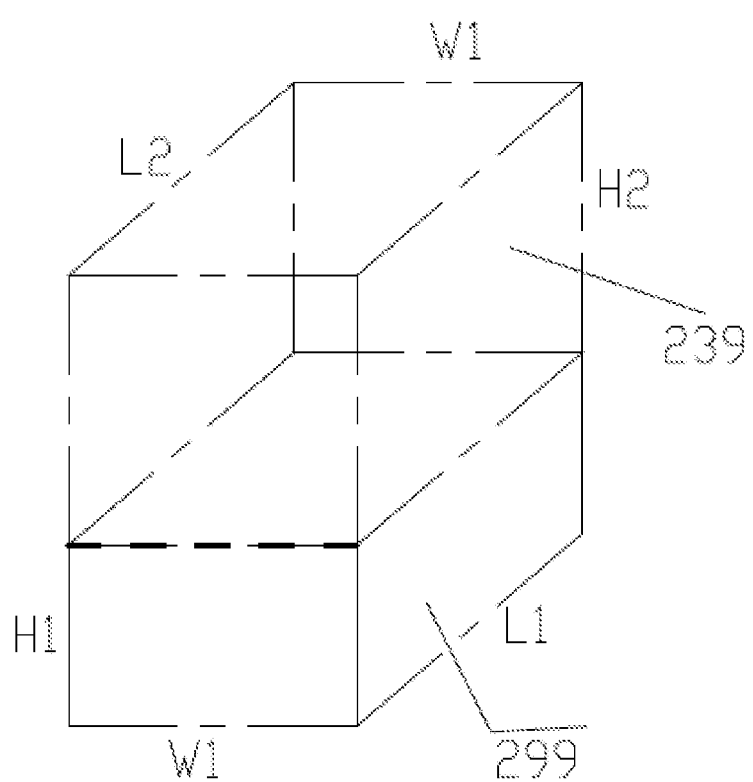
FIG. 6 shows a schematic view of a movement area of a permanent magnet above a subject under the control of the pneumatic balance arm.

FIG. 6 shows a schematic view of the movement area of the permanent magnet 230 above the subject under the control of the pneumatic balance arm 210. At this time, the movement area 239 of the permanent magnet 230 is above the area 299 where the subject is located, as shown in FIG. 6. The length of the digestive tract L1, the digestive tract width W1, and the digestive tract height H1 of the subject to be examined can be seen in FIG. 6. The width W2 of the movement range 239 of the permanent magnet 230 is substantially equal to the width W1 of the digestive tract, the length L2 of the movement range 239 is equivalent to the length L1 of the digestive tract, and the height H2 of the movement range 239 is the distance from the human body to a point where the capsule endoscope in digestive tract is out of control of the permanent magnet 230.

Figure 7:
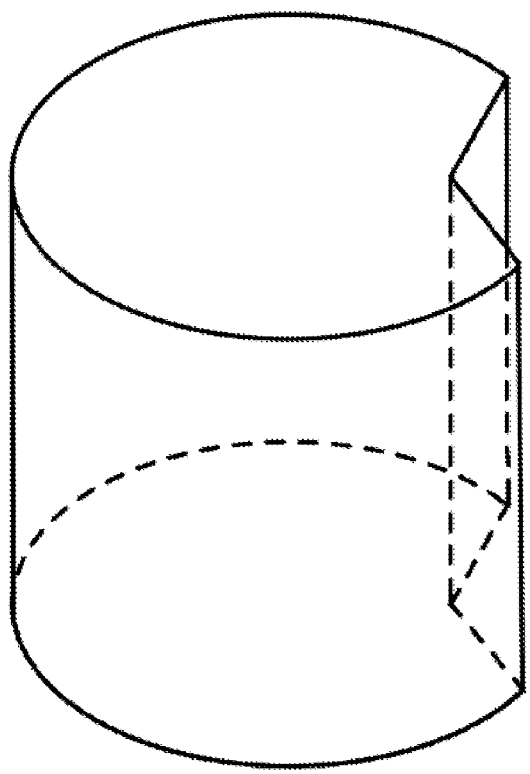
FIG. 7 shows a schematic view of an effective reachable area of the permanent magnet under the combined action of the pneumatic balance arm and the 2-DOF rotary platform, as examined from one side of the subject.

In one embodiment, FIG. 7 shows a schematic view of the effective reachable area of the permanent magnet under the combined action of the pneumatic balance arms 110 and 210 and the 2-DOF rotary platform 140 and 240, as examined from one side of the subject. Wherein, in one implementation, the triangular area is an area the permanent magnet can not reach. As shown in FIG. 7, under the combined action of the pneumatic balance arms 110 and 210 and the 2-DOF rotary platforms 140 and 240, the permanent magnet can reach the omni-directional area around the human digestive tract. Compared to the prior art, the examinable area has been significantly expanded, which is conducive to improving the examination accuracy and range.

Figure 8:
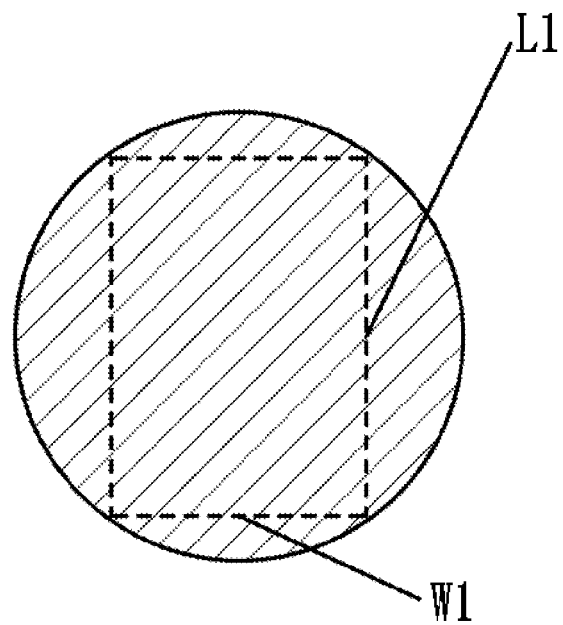
FIG. 8 shows a schematic view of the effective reachable area of the permanent magnet as examined from above of the subject.

In another embodiment, FIG. 8 shows a schematic view of the effective reachable area of the permanent magnet as examined from above the subject. As shown in FIG. 8, the rectangular area is a planar area formed by the digestive tract length L1 and the width W1 of the subject to be examined. The shaded area including both the circular area and the rectangular area is the effective reachable area of the permanent magnet.

Figure 9:
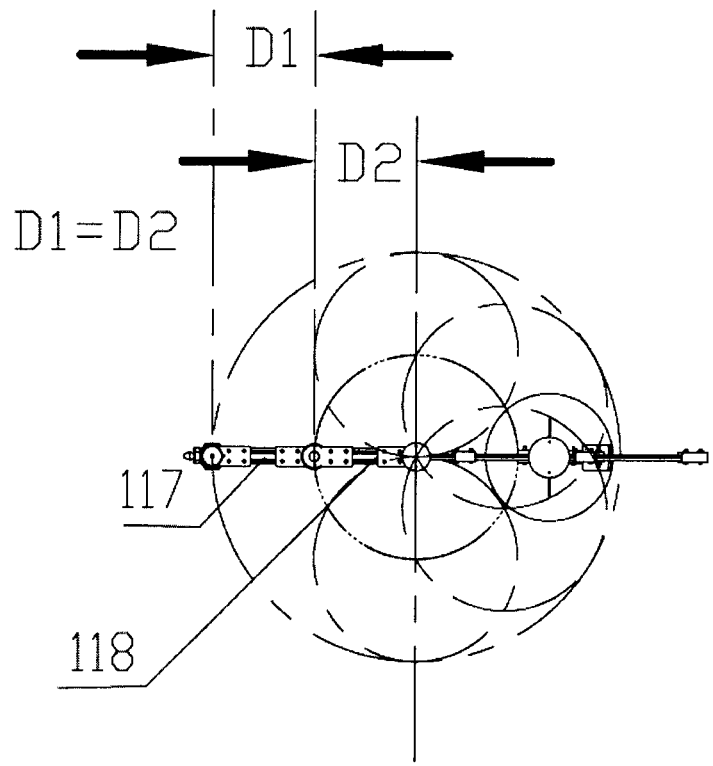
FIG. 9 shows a top schematic view of the effective reachable area of the permanent magnet.

In still another embodiment, FIG. 9 shows a top schematic view of the effective reachable area of the permanent magnet. As shown in FIG. 9, the upper balance arm, the rear terminal arm and the front terminal arm of the pneumatic balance arm pass through the center line, and the dashed circle in FIG. 9 represents the area where each of the parts can reach. Since the upper balance arm and the rear terminal arm are connected by a pivot that can rotate 360 degrees, and the rear terminal arm and the front terminal arm are also connected by a pivot that can rotate 360 degrees, the effective area where the permanent magnet can reach driven by the pneumatic balance arm is the outermost large circular area. As shown in FIG. 9, the length of the rear terminal arm is D2, and the length of the front terminal arm is D1. In one embodiment of the present invention, D1=D2, that is, the lengths of the front terminal arm and the rear terminal arm are equal. Therefore, the area reachable by the rear terminal arm and the front terminal arm is basically symmetrical along the axis, and can cover all regions of the human digestive tract, avoiding that certain regions cannot be examined because of length.

Since the detection area of the control device of the present invention is wide, as shown in FIGS. 6~9, the subject can also sit on the examination bed not limited to lying posture during clinical use. When a sitting posture or a standing posture is selected, the operator can perform an examination around the digestive tract of the subject by manually operating the 2-DOF rotary platform, which can also achieve the intended purpose.

FIG. 15 shows a schematic view of the spring assisted balance arm 310. The spring assisted balance arm 310 comprises a base 312 for providing support. The base 312 has its bottom fixed, and can be wall-mounted that is fixed on a wall surface (as shown in FIG. 15), or ceiling-mounted that is hung and fixed on the ceiling (not shown in FIG. 15). The spring assisted balance arm 310 further comprises a horizontal swing arm 313 connected to the top of the base 312. The other end of the horizontal swing arm 313 is connected with an upper balance arm 314, a lower balance arm 315, and a spring 316 that are angled with the horizontal swing arm 313. The upper balance arm 314 and the lower balance arm 315 are parallel to each other, and the spring 316 is used to provide impetus for the upper balance arm 314 and the lower balance arm 315 to move upward or downward through deformation thereof. Under the action of the spring 316, the upper balance arm 314 and the lower balance arm 315 can move 360 degrees vertically and horizontally. The spring 316 may be an common spring or a gas spring.

Wherein, the horizontal swing arm 313 is pivotally connected to the base 312, and is also pivotally connected to the upper balance arm 314 and the lower balance arm 315. The horizontal swing arm 313 can rotate 360 degrees horizontally along the pivot. The boom 311 is vertically connected to the other end of the upper balance arm 314, the lower balance arm 315 and the spring 316. In the embodiment, the upper balance arm 314, the lower balance arm 315, and the horizontal swing arm 313 are all rigid arms.

In this way, the rigid arm of the spring assisted balance arm 310 can bear the weight of the permanent magnet 130 fixed at the end of the boom 311 and overcome the gravity to move the permanent magnet 130 up and down, left and right, and achieve gravity balancing.

Figure 17:
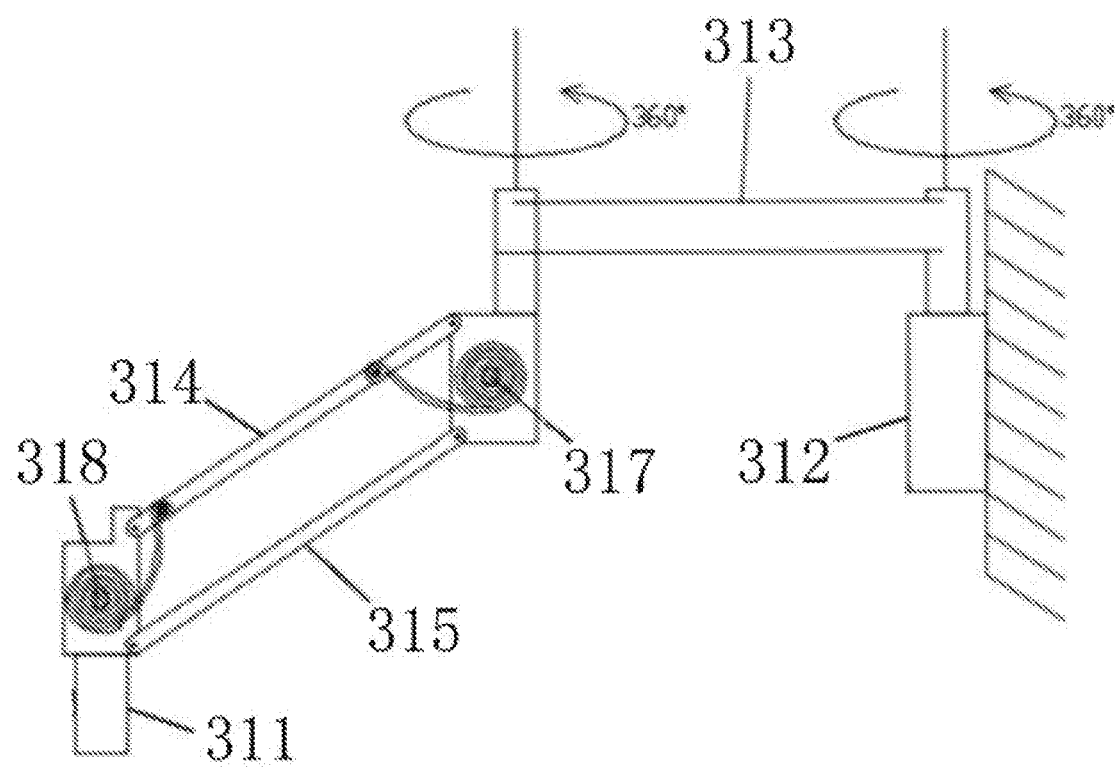
FIG. 17 is a schematic view showing the structure of a spring assist arm device of another embodiment.

As shown in FIG. 17, the present invention also discloses another embodiment. In the present another embodiment, the spring assist balance arm 310 includes a base 312 for providing support, and the base 312 is fixed at the bottom. The spring assist balance arm 310 further includes a horizontal swing arm or a yaw arm 313 coupled to the top end of the base 312. The other end of the horizontal swing arm or a yaw arm 313 is provided with an upper balance arm 314, a lower balance arm 315, and an upper portion at an angle to the horizontal swing arm or yaw arm 313, an upper coil spring 317, and lower coil spring 318. The upper balance arm 314 and the lower balance arm 315 are parallel to each other. The upper coil spring 317 is disposed at one end of the horizontal swing arm or yaw arm 313. The lower coil spring 318 is disposed at one end of the boom 311. Then through the deformation of the upper coil spring 317 and the lower coil spring 318, the upper balance arm 314 and the lower balance arm 315 move upwardly or downwardly. Under the influence of the upper coil spring 317 and the lower coil spring 318, the upper balance arm 314 and the lower balance arm 315 can deflect 360 degrees in the up and down and horizontal directions.

Figure 19:
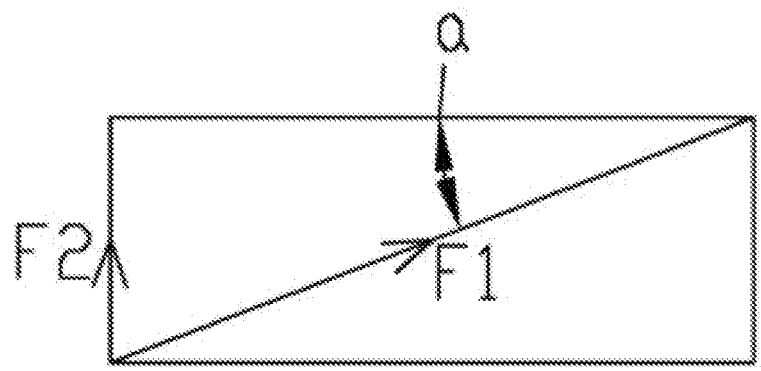
FIG. 19 is a schematic view showing a direction of a force generated by the deformation of a common spring, gas spring or coil spring.

In the present application, the common spring, the upper coil spring, the lower coil spring or the gas spring are used to balance the load and reduce the force demand on the manpower or the mechanical arm motor. As shown in FIG. 19, after the springs are deformed, spring forces F1 and F2 are generated in two directions. The spring forces F1 and F2 act on the upper balance arm and the lower balance arm, F2=sin α×F1, in common, F2 is used for balance for the load.

The mounting position of the magnetic sensor array 160 is determined based on the mounting position of the base 312. When the base 312 is wall-mounted, the magnetic sensor array 160 is also mounted on the wall surface near the base 312. When the base 312 is ceiling-mounted, the magnetic sensor array 160 is also mounted on the ceiling near the base 312.

Compared to the prior art, in the present invention, firstly, the gravity of the 2-DOF rotary platform 140, 240 and the permanent magnet 130, 230 is entirely supported by the pneumatic balance arm 110 and 210 or the spring assisted balance arm 310, which can greatly reduce the cost of precision mechanical arm of the prior art (usually the cost of the robotic arm is millions).

Secondly, the present invention provides a pneumatic balance arm 110 and 210 or a spring assisted balance arm 310 which solves the all-round movement of the permanent magnet 130 and 230 in the area above the subject, and rotation of the boom 111 drives the permanent magnet 130 and 230 below to realize accurate positioning with no dead corner in the entire area above the digestive tract of the subject, thereby improving examination accuracy.

Further, the 2-DOF rotary platform 140 and 240 drives the permanent magnet 130 and 230 to rotate horizontally and vertically, providing a 2-DOF rotation positioning in the horizontal and vertical directions, and this is manually controlled, ensuring a simple structure and effort-saving operation, with operation intensity and electromagnetic emission reduced.

In addition, in combination with the 2-DOF rotary platform, the control device for the capsule endoscope disclosed in the present invention realizes a simple transfer of human-permanent magnet, which makes the system simpler, and enables the permanent magnet to move in the area around the subject, more fitting to the human body, so that the control of the capsule endoscope is more direct and effective.

As a result, the control device for the capsule endoscope uses a balance arm device in conjunction with a 2-DOF rotary platform to provide a 5-DOF movement range, and realize free control of the capsule endoscope through control of the permanent magnet. In addition, the combination of a balance arm device and a manual 2-DOF rotary platform features simple structure, low effort and no electromagnetic emission, thereby achieving low-cost and high-precision of the entire system.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in particular the matters of shape, size and arrangement of parts within the principles of the present disclosure, up to and including the full extent established by the broad general meaning of the terms used in the claims.

What is claimed is:

1. A control device for a capsule endoscope, comprising:
a balance arm device, a permanent magnet and an examination bed;
wherein
the balance arm device comprises a column;
the balance arm device has
a fixed end which is fixed to a surface via an end of the column;
and
an active end of the balance arm device connects with a boom;
the permanent magnet is fixed under the boom;
the examination bed is positioned under the permanent magnet, and
an area between the examination bed and the permanent magnet is an examination area; and
a 2-DOF rotary platform, fixed below the boom and located above the permanent magnet,
wherein
when the 2-DOF rotary platform is moved horizontally in reference to a geodetic coordinate system,
a compensation in a horizontal angle is calculated and applied to the permanent magnet to prevent an undesired deflection of the permanent magnet in reference to a geodetic coordinate system, said undesired deflection is a result of the horizontal movement of 2-DOF rotary platform in reference to the geodetic coordinate system.

2. The control device of claim 1, wherein the balance arm device is a pneumatic balance arm, comprising a column and a chassis for support purpose, and the top of the column connects with an upper balance arm and a lower balance arm parallel to each other.

3. The control device of claim 2, wherein the pneumatic balance arm further comprises a balance cylinder and a control box fixed on one side of the column, wherein the control box is electrically connected to the balance cylinder, and the balance cylinder is connected to the upper balance arm and the lower balance arm via a piston; wherein the control box controls the balance cylinder and drives the upper balance arm and the lower balance arm to move in vertical direction.

4. The control device of claim 2, wherein the other ends of the upper balance arm and the lower balance arm connects with a rear terminal arm and a front terminal arm, wherein the rear terminal arm is located between the front terminal arm and the upper balance arm and the lower balance arm, wherein the upper balance arm, the lower balance arm, the rear terminal arm and the front terminal arm are rigid arms.

5. The control device of claim 4, wherein the rear terminal arm and the front terminal arm come with same or different lengths.

6. The control device of claim 4, wherein the rear terminal arm is pivotally connected to the upper balance arm and the lower balance arm, and the rear terminal arm is rotatable 360 degrees horizontally along a pivot.

7. The control device of claim 4, wherein the front terminal arm is pivotally connected to the rear terminal arm, and the front terminal arm is rotatable 360 degrees horizontally along a pivot.

8. The control device of claim 4, wherein the boom is fixed at the other end of the front terminal arm and is vertically connected to the front terminal arm.

9. The control device of claim 1, wherein the 2-DOF rotary platform is a full-manual rotary platform, comprising an upper enclosure, wherein the upper enclosure is symmetrical along a central axis and comprises a horizontal part and two vertical parts that are perpendicular to the horizontal part, wherein a bearing passing through the central axis is fitted at the horizontal part and provides 360-degree rotation in the horizontal direction, wherein each vertical part is fitted with a bearing and a horizontal rod passes through the bearings, two handles are fitted on both ends of the horizontal rod, and the permanent magnet is sleeved on the horizontal rod.

10. The control device of claim 9, wherein the 2-DOF rotary platform comprises a first enclosure and a second enclosure, a first motor fixed in the first enclosure provides a 360-degree rotation along a longitudinal axis, and a second motor fixed in the second enclosure provides a 360-degree rotation along a horizontal axis.

11. The control device of claim 10, wherein a control handle is fitted on one side of the first enclosure, and the control handle provides a horizontal rotation button and a vertical rotation button to control the permanent magnet to rotate horizontally or vertically.

12. The control device of claim 1, further comprising a magnetic sensor array, wherein the magnetic sensor array comprises a plurality of magnetic sensors, and the magnetic sensor array detects the spatial position of the permanent magnet through the plurality magnetic field sensors to obtain a three-dimensional position and a two-dimensional direction of the permanent magnet.

13. The control device of claim 12, wherein the magnetic sensor array calculates a compensation angle of the 2-DOF rotary platform according to a displacement of the permanent magnet.

14. The control device of claim 12, wherein
the magnetic sensor array detects a horizontal movement direction of the permanent magnet and a rotation of the permanent magnet caused by the horizontal movement of the 2-DOF rotary platform, the undesired deflection of the permanent magnet in reference to the geodetic coordinate system is characterized, and a compensation rotation is calculated and applied to the permanent magnet.

15. The control device of claim 1, wherein the permanent magnet controls the movement of the capsule endoscope in a digestive tract,
when the capsule endoscope is on the lower wall of the digestive tract, a tangential direction of the permanent magnet rotating away from the lower gastric wall is opposite to the movement direction of the permanent magnet; and
when the capsule endoscope is at the upper gastric wall of the digestive tract a tangential direction of the permanent magnet rotating away from the upper gastric wall is consistent with the movement direction of the permanent magnet.

16. The control device of claim 1, wherein the rotation and movement speed of the permanent magnet follows $v=\omega*L$, wherein v is the average movement speed of the permanent magnet, $\omega$ is the average rotation angular speed of the permanent magnet, and L is the length of the capsule endoscope.

17. The control device of claim 1, wherein the balance arm device is a spring assisted balance arm, comprising
a base for providing support and a horizontal swing arm connected to a top of the base,
wherein an other end of the horizontal swing arm connects with an upper balance arm, a lower balance arm, and a spring that are angled with the horizontal swing arm, the upper balance arm and the lower balance arm are parallel to each other, and the spring provides impetus for the upper balance arm and the lower balance arm to move upward or downward through deformation.

18. The control device of claim 17, wherein the spring is a common spring or a gas spring.

19. The control device of claim 17, wherein the horizontal swing arm is pivotally connected to the base, and is also pivotally connected to the upper balance arm and the lower balance arm, wherein the horizontal swing arm rotate 360 degrees horizontally along a pivot.

20. The control device of claim 17, wherein the boom is vertically connected to the other end of the upper balance arm, the lower balance arm and the spring.

21. The control device of claim 17, wherein the upper balance arm, the lower balance arm, and the horizontal swing arm are rigid arms.

22. The control device of claim 17, wherein the spring comprises an upper coil spring and a lower coil spring, and the upper coil spring is disposed at one end of the horizontal swing arm, and the lower coil spring is disposed at one end of the boom, the upper coil spring and the lower coil spring can provide impetus for the upper balance arm and the lower balance arm to move upward or downward through deformation.

23. The control device of claim 1, wherein the permanent magnet rotates at one or more degrees of freedom.

* * * * *